United States Patent [19]

Schaus et al.

[11] Patent Number: 5,389,687
[45] Date of Patent: Feb. 14, 1995

[54] RING-SUBSTITUTED 2-AMINO-1,2,3,4-TETRA-HYDRONAPHTHALENES

[75] Inventors: John M. Schaus; Robert D. Titus, both of Indianapolis, Ind.

[73] Assignee: Eli Lilly and Company, Indianapolis, Ind.

[21] Appl. No.: 683,637

[22] Filed: Apr. 11, 1991

Related U.S. Application Data

[63] Continuation of Ser. No. 315,750, Feb. 27, 1989, abandoned.

[51] Int. Cl.$^6$ .................... A61K 31/135; C07C 211/38
[52] U.S. Cl. ........................... 514/657; 514/656; 564/426; 564/428
[58] Field of Search .................... 564/428, 429, 426; 514/657, 656, 821

[56] References Cited

U.S. PATENT DOCUMENTS

| | | | |
|---|---|---|---|
| 3,930,022 | 12/1975 | Hauck et al. | 514/657 |
| 4,442,126 | 4/1984 | Beeley et al. | 514/657 |
| 4,873,262 | 10/1989 | Junge et al. | 514/510 |
| 4,876,284 | 10/1989 | Arvidsson et al. | 514/657 |

FOREIGN PATENT DOCUMENTS

| | | | |
|---|---|---|---|
| 637363A | 7/1983 | Czechoslovakia | 564/428 |
| 272534A | 6/1988 | European Pat. Off. | |

OTHER PUBLICATIONS

*Goodman and Gilman's, The Pharmacological Basis of Therapeutics,* 7th ed., pp. 482, 483 and 784–793 (1985).

Primary Examiner—Shailendra Kumar
Attorney, Agent, or Firm—Douglas J. Taylor

[57] ABSTRACT

The present invention provides novel ring-substituted 2-amino-1,2,3,4-tetrahydronaphthalenes which exhibit binding activity at the serotonin 1A receptor.

19 Claims, No Drawings

RING-SUBSTITUTED 2-AMINO-1,2,3,4-TETRA-HYDRONAPHTHALENES

This application is a continuation of application Ser. No. 07/315,750, filed Feb. 27, 1989, now abandoned.

BACKGROUND OF THE INVENTION

Over the last several years it has become apparent that the neurotransmitter serotonin (5-hydroxytryptamine—5-HT) is associated directly or indirectly with a number of physiological phenomena, including appetite, memory, thermoregulation, sleep, sexual behavior, anxiety, depression, and hallucogenic behavior [Glennon, R. A., *J. Med. Chem.* 30, 1 (1987)].

It has been recognized that there are multiple types of 5-HT receptors. These receptors have been classified as $5\text{-}HT_1$, $5\text{-}HT_2$, and $5\text{-}HT_3$ receptors, with the former being further divided into the sub-classes $5\text{-}HT_{1A}$, $5\text{-}HT_{1B}$, $5\text{-}HT_{1C}$, and $5\text{-}HT_{1D}$.

We have now discovered a class of compounds which exhibit high binding affinity at the $5\text{-}HT_{1A}$ receptor. The compounds, by reason of their $5\text{-}HT_{1A}$ agonist activity, are useful in the treatment, for example, of sexual dysfunction, anxiety, depression, and eating disorders, such as anorexia.

SUMMARY OF THE INVENTION

The present invention provides novel ring-substituted 2-amino-1,2,3,4-tetrahydronaphthalenes which are selective agonists at the $5\text{-}HT_{1A}$ receptor.

More specifically, this invention relates to a compound of the formula

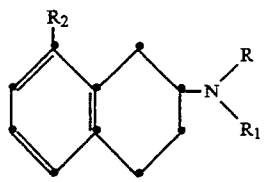

in which R is $C_1\text{-}C_4$ alkyl or allyl;

$R_1$ is hydrogen, $C_1\text{-}C_4$ alkyl, or allyl;

$R_2$ is formyl, cyano, halo, hydroxymethyl, carboxamido, $CO_2R_3$, or $NHCOR_3$ in which $R_3$ is hydrogen or $C_1\text{-}C_4$ alkyl;

and pharmaceutically acceptable acid addition salts thereof.

This invention also provides a pharmaceutical formulation which comprises, in association with a pharmaceutically acceptable carrier, diluent, or excipient, a compound of the formula

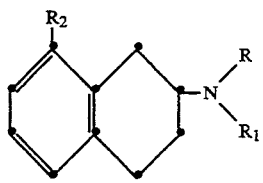

in which R is $C_1\text{-}C_4$ alkyl or allyl;

$R_1$ is hydrogen, $C_1\text{-}C_4$ alkyl, or allyl;

$R_2$ is formyl, cyano, halo, hydroxymethyl, carboxamido, $CO_2R_3$, or $NHCOR_3$ in which $R_3$ is hydrogen or $C_1\text{-}C_4$ alkyl;

and pharmaceutically acceptable acid addition salts thereof.

A further embodiment of the invention is a method for effecting a biological response at the $5\text{-}HT_{1A}$ receptor. More particularly, further embodiments are methods for treating a variety of disorders which have been linked to decreased activation of the $5\text{-}HT_{1A}$ site in mammals. Included among these disorders are anxiety, depression, sexual dysfunction, and eating disorders.

In addition, the compounds of this invention exhibit activity in lowering blood pressure and reducing heart rate, and, thus, further embodiments of this invention are methods for lowering blood pressure and for reducing heart rate.

Any of these methods employ a compound of the formula

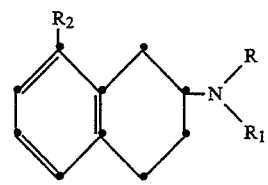

in which R is $C_1\text{-}C_4$ alkyl or allyl;

$R_1$ is hydrogen, $C_1\text{-}C_4$ alkyl, or allyl;

$R_2$ is formyl, cyano, halo, hydroxymethyl, carboxamido, $CO_2R_3$, or $NHCOR_3$ in which $R_3$ is hydrogen or $C_1\text{-}C_4$ alkyl;

and pharmaceutically acceptable acid addition salts thereof.

Another embodiment of this invention is a process for producing certain of the compounds of this invention. The process is directed to the production of a compound of the formula

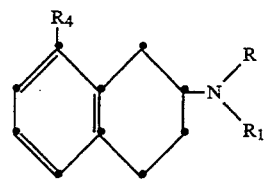

in which R is $C_1\text{-}C_4$ alkyl, allyl;

$R_1$ is hydrogen, $C_1\text{-}C_4$ alkyl, allyl;

$R_4$ is formyl, carboxamido, or $CO_2R_3$ in which $R_3$ is hydrogen or $C_1\text{-}C_4$ alkyl;

and comprises reacting a compound of the formula

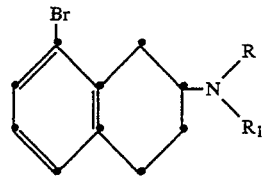

in which R and $R_1$ are as hereinabove defined, with an alkyl lithium to produce the corresponding 8-lithio compound, and then reacting the resulting 8-lithio compound with an appropriate electrophile selected from the group consisting of a formamide, an isocyanate, and a haloformate ester.

DETAILED DESCRIPTION OF THE INVENTION

In the above formulas, the term "$C_1$-$C_4$ alkyl" means a straight or branched alkyl chain having from one to four carbon atoms. Such $C_1$-$C_4$ alkyl groups are methyl, ethyl, n-propyl, isopropyl, n-butyl, isobutyl, sec-butyl, and t-butyl.

The term "halo" means fluoro, chloro, bromo, or iodo.

While all of the compounds of the present invention are useful for treating a variety of disorders which have been linked to decreased activation of the 5-$HT_{1A}$ receptor in mammals, certain of the compounds are preferred.

R and $R_1$ preferably are both $C_1$-$C_4$ alkyl, and, more preferably, both R and $R_1$ are n-propyl.

$R_2$ preferably is carboxamido, chloro, bromo, or $CO_2R_3$ in which $R_3$ is $C_1$-$C_4$ alkyl.

The compounds of the present invention possess an asymmetric carbon represented by the carbon atom labeled with an asterisk in the following formula:

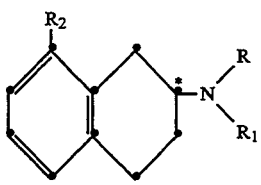

As such, each of the compounds exists as its individual d- and l-stereoisomers as well as the racemic mixture of such isomers. Accordingly, the compounds of the present invention include not only the dl-racemates but also their respective optically active d- and l-isomers.

As-mentioned hereinabove, the invention includes pharmaceutically acceptable acid addition salts of the compounds defined by the above formula. Since the compounds of this invention are amines, they are basic in nature and accordingly react with any of a number of inorganic and organic acids to form pharmaceutically acceptable acid addition salts. Since the free amines of the compounds of this invention are typically oils at room temperature, it is preferable to convert the free amines to their corresponding pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisullite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid.

In addition, some of these salts may form solvates with water or organic solvents such as ethanol. Such solvates also are included as compounds of this invention.

The following compounds further illustrate compounds contemplated within the scope of this invention:

2-(Di-n-propylamino)-8-formyl-1,2,3,4-tetrahydronaphthalene;

2-Ethylamino-8-bromo-1,2,3,4-tetrahydronaphthalene;

2-(N-Methyl-N-isopropylamino)-8-formamido-1,2,3,4-tetrahydronaphthalene;

2-Di-n-butylamino-8-hydroxymethyl-1,2,3,4-tetrahydronaphthalene;

2-Diethylamino-8-cyano-1,2,3,4-tetrahydronaphthalene;

2-(Di-n-propylamino)-8-chloro-1,2,3,4-tetrahydronaphthalene;

2-Dimethylamino-8-carboxamido-1,2,3,4-tetrahydronaphthalene;

2-(Di-n-propylamino)-8-carboxy-1,2,3,4-tetrahydronaphthalene;

2-Dimethylamino-8-ethoxycarbonyl-1,2,3,4-tetrahydronaphthalene;

2-(Di-isobutylamino)-8-acetamido-1,2,3,4-tetrahydronaphthalene;

2-(Di-n-propylamino)-8-iodo-1,2,3,4-tetrahydronaphthalene;

2-n-Propylamino-8-propionamido-1,2,3,4-tetrahydronaphthalene;

2-n-Butylamino-8-methoxycarbonyl-1,2,3,4-tetrahydronaphthalene;

2-(Di-n-propylamino)-8-fluoro-1,2,3,4-tetrahydronaphthalene;

2-(Di-n-propylamino)-8-propoxycarbonyl-1,2,3,4-tetrahydronaphthalene; and the like.

The compounds of the present invention may be prepared by procedures well known to those of ordinary skill in the art. These compounds preferably are synthesized via an 8-substituted-2-tetralone. The 8-substituted-2-tetralone is reductively aminated with the desired amine. When the 8-substituent is bromo, it can be conveniently replaced with an alternate desired substituent either by copper-assisted displacement by a nucleophile or by lithiation followed by reaction with an electrophile.

Schemes for these reactions are as follows:

A. Synthesis of 8-Substituted-2-tetralone

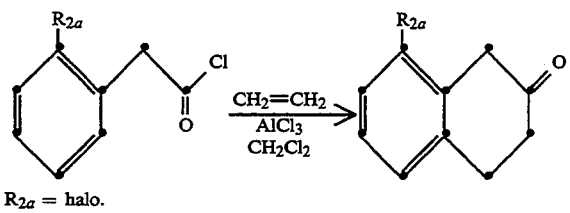

$R_{2a}$ = halo.

B. Reductive Amination

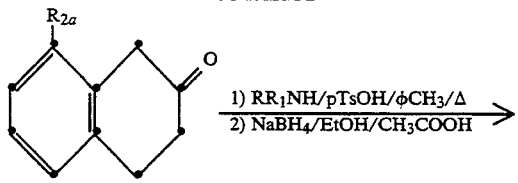

1) RR₁NH/pTsOH/φCH₃/Δ
2) NaBH₄/EtOH/CH₃COOH

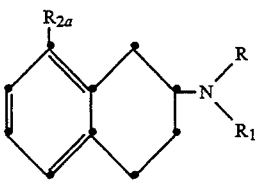

C. Replacement of Bromo Ring Substituent Via Lithiation

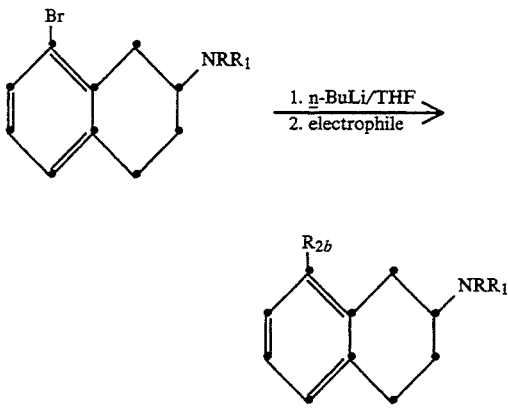

1. n-BuLi/THF
2. electrophile

| Electrophile | R$_{2b}$ |
|---|---|
| dimethylformamide | CHO |
| trimethylsilylisocyanate | CONH$_2$ |
| alkyl chloroformate | CO$_2$R$_3$ |

D. Replacement of Bromo Ring Substituent via Copper Assisted Nucleophilic Displacement.

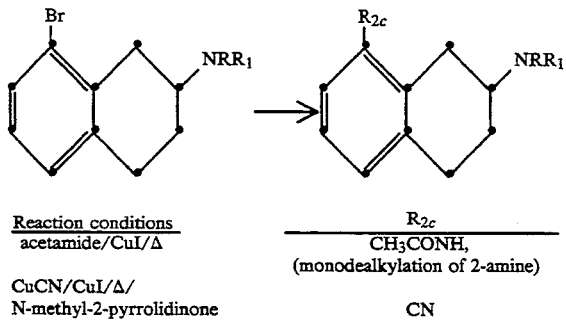

| Reaction conditions | R$_{2c}$ |
|---|---|
| acetamide/CuI/Δ | CH$_3$CONH, (monodealkylation of 2-amine) |
| CuCN/CuI/Δ/ N-methyl-2-pyrrolidinone | CN |

As depicted above, the 8-bromo-2-aminotetralin represents an intermediate which, by an appropriate displacement reaction, leads to other compounds of this invention. Those compounds of this invention in which R$_2$ is hydroxymethyl are available by reduction of the corresponding 8-formyl compound. The reduction typically is carried out using sodium borohydride.

Those compounds of this invention in which R$_2$ is a carboxamide group are available by hydrolysis of the corresponding 8-cyano compound. The hydrolysis is typically carried out using polyphosphoric acid.

The basic starting tetralones are available by any of a wide range of recognized methods. For example, they can be produced by a Friedel-Crafts reaction of an appropriately ring-substituted phenylacetyl chloride with ethylene in the presence of aluminum chloride.

The tetralone, once formed, can, by simple reductive amination using the selected amine, be converted to a 2-amino-8-substituted-1,2,3,4-tetrahydronaphthalene compound of this invention. The tetralone is first reacted with the amine to form the corresponding enamine after which the enamine is reduced with sodium borohydride to the tetrahydronaphthalene.

The 2-amino-8-bromo-1,2,3,4-tetrahydronaphthalene can be used to produce other compounds of this invention by formation of a lithium intermediate via a lithiation reaction using n-butyllithium. The reactive lithium intermediate is treated with an appropriate electrophile to give compounds of this invention.

Alternatively, the 2-amino-8-bromo-1,2,3,4-tetrahydronaphthalene may be treated with a nucleophile in the presence of a copper salt to produce compounds of this invention.

The optically active isomers of the racemates of the invention are also considered part of this invention. Such optically active isomers may be prepared from their respective optically active precursors by the procedures described above, or by resolving the racemic mixtures. This resolution can be carried out in the presence of a resolving agent, by chromatography or by repeated crystallization. Particularly useful resolving agents are d- and l-tartaric acids, d- and l-ditoluoyltartaric acids, and the like.

Another method for producing optically active isomers of the compounds of this invention involves the use of an α-phenethylamine. As described above, the compounds of this invention generally and conveniently are produced via an 8-substituted-2-tetralone. The tetralone intermediate may be reductively aminated with an optically active α-phenethylamine after which the resulting mixture of optical isomers is separated by recognized methodology, such as chromatography. Cleavage of the α-phenethyl moiety produces a correspondingly substituted, optically active 2-amino-1,2,3,4-tetrahydronaphthalene.

The conditions necessary for removing the phenethyl moiety are relatively severe and can tend to disrupt the integrity of the core tetralin molecule. It has been discovered that the cleavage can be carried out in a much more facile and efficient manner requiring only mild cleavage conditions when the particular α-phenethylamine which is used is p-nitro-α-phenethylamine.

Cleavage of the p-nitro-α-phenethyl moiety in accordance with the present invention is achieved by reduction of the p-nitro group followed by acid-catalyzed solvolysis of the resulting p-amino-α-phenethyl moiety. Reduction of the nitro group can be accomplished by a wide range of reducing agents including, for example, titanium trichloride, lithium aluminum hydride, or zinc/acetic acid, or by catalytic hydrogenation. Solvolytic cleavage takes place when the monohydrochloride (or other monobasic salt) of the reduction product is treated with water or an alcohol at room temperature or, in some instances, at elevated temperatures. A particularly convenient condition for removing the p-nitro-α-phenethyl moiety is hydrogenation of the amine monohydrochloride in methanol over a platinum catalyst.

The compounds employed as starting materials in the synthesis of the compounds of this invention are well known and readily synthesized by standard procedures commonly employed by those of ordinary skill in the art.

The pharmaceutically acceptable acid addition salts of the invention are typically formed by reacting a 1,2,3,4-tetrahydronaphthalene of this invention with an equimolar or excess amount of acid. The reactants are generally combined in a mutual solvent such as diethyl ether or benzene, and the salt normally precipitates out of solution within about one hour to 10 days, and can be isolated by filtration.

The following Examples further illustrate the compounds of the present invention and methods for their synthesis. The Examples are not intended to be limiting to the scope of the invention in any respect and should not be so construed.

EXAMPLE 1

Preparation of 2-Di-n-propylamino-8-chloro-1,2,3,4-tetrahydronaphthalene.

To a solution of 8-chloro-2-tetralone (3.0 gm, 16.6 mMol) in benzene (25 mL) were added dipropylamine (3.35 mL, 33.2 mMol) and p-toluenesulfonic acid (100 mg), and the reaction mixture was heated at reflux for 4 hours with constant water removal (Dean-Stark trap). The reaction mixture was then cooled to room temperature, and the volatiles were removed in vacuo to give a dark viscous residue. To a solution of this crude material in methanol (30 mL) were added acetic acid (3 mL) followed by the dropwise addition of sodium borohydride (1.5 gm) in ethanol (60 mL) with cooling. The reaction mixture was stirred for 18 hours at room temperature. To this was then added hydrochloric acid (6M, 20 mL) and the mixture stirred 4 hours at room temperature. The volatiles were then removed in vacuo and the residue triturated with water. The aqueous phase was extracted once with diethyl ether, and the organic phase was discarded. The remaining aqueous phase was made basic with concentrated ammonium hydroxide and was then extracted well with dichloromethane. The organic extracts were combined, washed with saturated aqueous sodium chloride, dried over sodium sulfate and concentrated in vacuo to give an orange liquid. Purification by chromatography on basic alumina (Activity I, dichloromethane) gave a colorless liquid (1.75 gm, 40%). The hydrochloride salt was formed and recrystallized (ethanol/diethyl ether) to give a colorless, crystalline-solid (m.p.=159°-160° C.).

Analysis: Calculated for $C_{16}H_{24}NCl \cdot HCl$: Theory: C, 63.57, H, 8.34, N, 4.63; Found: C, 63.79, H, 8.46, N, 4.57.

EXAMPLE 2

Preparation of 2-Diethylamino-8-chloro-1,2,3,4-tetrahydronaphthalene.

To a solution of 8-chloro-2-tetralone (500 mg, 2.78 mMol) in cyclohexane (25 mL) were added diethylamine (1.4 mL, 13.9 mMol) and p-toluenesulfonic acid, and the reaction mixture was heated at reflux for 18 hours with constant water removal (Dean-Stark trap). The reaction mixture was then cooled to room temperature, and the volatiles were removed in vacuo to give a dark residue. To a solution of this dark residue in methanol (15 mL) were added acetic acid (1.5 mL) followed by sodium borohydride (500 mg) in portions. The mixture was stirred for one hour at room temperature. The reaction mixture was then diluted with 10% hydrochloric acid and stirred for one hour at room temperature. The aqueous solution was extracted once with diethyl ether, and the organic phase was discarded. The remaining aqueous phase was poured over ice, made basic with concentrated ammonium hydroxide and extracted well with dichloromethane. The organic extracts were combined, dried over sodium sulfate and concentrated in vacuo to give a dark oil. Purification on a basic alumina column (Activity I, dichloromethane) gave a colorless oil (200 mg 30%). The hydrochloride salt was formed, and recrystallization (acetone/diethyl ether) gave colorless crystals (m.p.=155°-156° C).

Analysis: Calculated for $C_{14}H_{20}NCl \cdot HCl$: Theory: C, 61.32; H, 7.72; N, 5.11; Found: C, 61.62; H, 7.94; N, 5.03.

EXAMPLE 3

Preparation of 2-Diallylamino-8-chloro-1,2,3,4-tetrahydronaphthalene.

To a solution of 8-chloro-2-tetralone (5.0 gm, 27.8 mMol) in toluene (50 mL) were added freshly distilled (b.p.=112° C.) diallylamine (7 mL, 56.7 mMol) and p-toluenesulfonic acid (500 mg), and the reaction mixture was stirred at reflux for 3 hours with constant water removal (Dean-Stark trap). The reaction mixture was then cooled to room temperature and volatiles removed in vacuo to give a brown-orange, viscous residue. To a solution of this residue in tetrahydrofuran (100 mL) was added sodium cyanoborohydride (3 gm, 47.7 mMol), and the resulting suspension was saturated with hydrogen chloride. The resulting mixture was stirred at room temperature for 18 hours. The reaction mixture was then poured into water (300 mL) and made basic with aqueous sodium hydroxide. After stirring for two hours at room temperature the reaction mixture was poured into ice and made strongly acidic with concentrated hydrochloric acid. The aqueous solution was extracted with diethyl ether and the organic phase discarded. The remaining aqueous was made strongly basic with aqueous sodium hydroxide and was extracted with dichloromethane. The combined organic extracts were dried over sodium sulfate and concentrated in vacuo to give a violet liquid. Purification on a basic alumina column (Activity I, dichloromethane) gave a colorless oil (1.7 gm, 24%). The hydrochloride salt was formed and recrystallized (ethanol/diethyl ether) to give a colorless solid (m.p.=117°-118° C.).

Analysis: Calculated for $C_{16}H_{20}NCl \cdot HCl$: Theory: C, 64.43, H, 7.10, N, 4.70; Found: C, 64.28, H, 7.25, N, 4.68.

EXAMPLE 4

Preparation of 2-Di-n-butylamino-8-chloro-1,2,3,4-tetrahydronaphthalene.

8-Chloro-2-tetralone (3 gm, 16.6 mMol) in toluene (25 mL) was reacted with dibutylamine (5.6 mL, 33.2 mMol) and sodium borohydride (2.0 gm) as described in Example 2 to give the title compound as a colorless oil (1.4 gm, 29%). The tosylate salt was formed and recrystallization (ethyl acetate) gave a colorless, crystalline solid (m.p.=73°-74° C.).

Analysis: Calculated for $C_{18}H_{28}NCl \cdot C_7H_8SO_3 \cdot H_2O$: Theory: C, 62.03, H, 7.91, N, 2.89; Found: C, 62.25, H, 7.69, N, 2.69.

EXAMPLE 5

Preparation of 2-Di-n-propylamino-8-bromo-1,2,3,4-tetrahydronaphthalene.

8-Bromo-2-tetralone (28.8 gm, 128 mMol) was reacted with dipropylamine (34.3 mL, 250 mMol) and sodium cyanoborohydride (6.3 gm, 100 mMol) as described in Example 3 to give the title compound as a light yellow oil. The hydrochloride salt was formed and crystallization (acetone) gave colorless crystals (m.p.=150.5°-152° C.).

Analysis: Calculated for $C_{16}H_{24}NBr \cdot HCl$: Theory: C, 55.42, H, 7.27, N, 4.04; Found: C, 55.65, H, 7.55, N, 3.82.

EXAMPLE 6

Preparation of 2-Di-n-propylamino-8-fluoro-1,2,3,4-tetrahydronaphthalene.

8-Fluoro-2-tetralone (2.60 gm, 15.8 mMol) was reacted with dipropylamine (3.3 mL, 33 mMol) and sodium borohydride (1.5 gm) as described in Example 1 to give the title compound as a colorless oil (1.3 gm, 33%). The hydrochloride salt was formed and crystallization (ethanol/diethyl ether) gave colorless crystals (m.p.=164° C.).

Analysis: Calculated for $C_{16}H_{24}NF \cdot HCl$:

Theory: C, 67.23, H, 8.82, N, 4.90; Found: C, 67.12, H, 8.72, N, 4.81.

EXAMPLE 7

Preparation of 2-Di-n-propylamino-8-methoxycarbonyl-1,2,3,4-tetrahydronaphthalene.

8-Methoxycarboxy-2-tetralone (1.11 gm, 5.4 mMol) was reacted with dipropylamine (2.5 mL, 25 mMol) and sodium borohydride (370 mg) as described in Example 1 to give the title compound as a colorless, viscous oil (580 mg, 37%). The hydrochloride salt was formed and crystallization (ethanol/diethyl ether) gave colorless crystals (m.p.=136° C.).

Analysis: Calculated for $C_{18}H_{27}NO_2 \cdot HCl$: Theory: C, 66.34, H, 8.66, N, 4.30; Found: C, 66.55, H, 8.59, N, 4.14.

Alternatively, to a solution of 8-bromo-2-dipropylamino-1,2,3,4-tetrahydronaphthalene (220 mg, 0.71 mMol) in tetrahydrofuran (5 mL) at $-78°$ C. was added a solution of n-butyl lithium in hexane (1.6 M, 1 mL, 1.6 mMol), and the solution was stirred for two hours at $-78°$ C. The solution was then cannulated into a solution of methyl chloroformate (0.5 mL, 6.5 mMol) in tetrahydrofuran (10 mL) at $-78°$ C., and the reaction mixture was allowed to warm gradually to room temperature. The reaction mixture was diluted with saturated aqueous sodium bicarbonate and was then extracted with diethyl ether. The combined extracts were dried over sodium sulfate and evaporated in vacuo to give a greenish-yellow oil. Purification by flash chromatography (3:1 hexane:tetrahydrofuran+tr. $NH_4OH$) gave the title compound as a colorless glass (130 mg, 63%). The hydrochloride salt was formed and recrystallized (acetone/diethyl ether) to give colorless crystals (m.p.=132° C.).

Analysis: Calculated for $C_{18}H_{27}NO_2 \cdot HCl$: Theory: C, 66.34, H, 8.66, N, 4.30; Found: C, 66.38, H, 8.89, N, 4.59.

EXAMPLE 8

Preparation of 2-Di-n-propylamino-8-cyano-1,2,3,4-tetrahydronaphthalene.

8-Cyano-2-tetralone (500 mg, 2.9 mMol) was reacted with dipropylamine (0.8 mL, 5.8 mMol) and sodium borohydride (370 mg) as described in Example 1 to give the title compound as a colorless, viscous oil (260 mg, 35%). The hydrochloride salt was formed and crystallization (ethanol/diethyl ether) gave colorless crystals (m.p.=175°-176° C.).

Analysis: Calculated for $C_{17}H_{24}N_2 \cdot HCl$: Theory: C, 69.72, H, 8.-60, N, 9.57; Found: C, 69.69, H, 8.75, N, 9.55.

EXAMPLE 9

Preparation of 2-Dimethylamino-8-cyano-1,2,3,4-tetrahydronaphthalene.

8-Cyano-2-tetralone (2 gm, 11.7 mMol) in acetonitrile (30 mL) with dimethylamine hydrochloride (5.72 gm, 70 mMol), sodium acetate (5.76 gm, 70 mMol), sodium cyanoborohydride (520 mg, 8.2 mMol) and 3A molecular sieves (1.2 gm) were stirred together for 4 days at room temperature. The reaction mixture was then diluted with conc. ammonium hydroxide and stirred for 4 hours. This mixture was extracted with dichloromethane. The organic extracts were combined, dried over sodium sulfate and concentrated in vacuo to give a dark oil. Purification on a basic alumina column (Activity I, 2% methanol in dichloromethane) gave a brown oil which was converted to its hydrochloride salt. Recrystallization (methanol/diethyl ether) gave colorless crystals (520 mg, m.p.=229°-230° C.).

Analysis: Calculated for $C_{13}H_{16}N_2 \cdot HCl$: Theory: C, 65.95, H, 7.24, N, 11.83; Found: C, 65.68, H, 7.46, N, 11.76.

EXAMPLE 10

Preparation of 2-n-Propylamino-8-chloro-1,2,3,4-tetrahydronaphthalene.

8-Chloro-2-tetralone (500 mg, 2.78 mMol) in toluene (25 mL) was reacted with propylamine (1.14 mL, 13.9 mMol) and sodium borohydride (500 rag) as described in Example2 to give after purification by flash chromatography (5% methanol in dichloromethane+tr. $NH_4OH$) the title compound as a dark oil (340 mg, 55%). The hydrochloride was formed, and recrystallization (ethanol/diethyl ether) gave a colorless, crystalline solid (m.p.=213°-215° C.).

Analysis: Calculated for $C_{13}H_{18}NCl \cdot HCl$: Theory: C, 60.01, H, 7.36, N, 5.38; Found: C, 60.22, H, 7.19, N, 5.59.

EXAMPLE 11

Preparation of 2-Dimethylamino-8-chloro-1,2,3,4-tetrahydronaphthalene.

A solution of 8-chloro-2-amino-1,2,3,4-tetrahydronaphthalene (250 mg, 1.4 mMol) in 90% formic acid (4 mL) which contained 37% aqueous formaldehyde (0.4 mL) was heated at 80° C. for 18 hours. The reaction mixture was then poured into cold water and made basic with concentrated ammonium hydroxide. The aqueous solution was extracted well with 3:1 chloroform:isopropanol. The combined organic extracts were washed with saturated aqueous sodium chloride, dried over sodium sulfate and concentrated in vacuo to give a yellow oil. Purification by flash chromatography ($-5\%$ methanol in dichloromethane+tr. $NH_4OH$) to give the title compound as a light yellow, oily solid (173 mg, 59%). The hydrochloride salt was formed and recrystallized (ethanol/diethyl ether) to give beige crystals (m.p.=207°-208° C.).

Analysis: Calculated for $C_{12}H_{16}NCl \cdot HCl$: Theory: C, 58.55, H, 6.96, N, 5.69; Found: C, 58.53, H, 7.02, N, 5.48.

EXAMPLE 12

Preparation of 2-Methylamino-8-chloro-1,2,3,4-tetrahydronaphthalene.

To a solution of 8-chloro-2-amino-1,2,3,4-tetrahydronaphthalene (250 mg, 1.38 mMol) in tetrahydrofuran (25 mL) was added triethylamine (0.38 mL, 2.76 mMol) followed by the careful addition of methyl chloroformate (0.26 mL, 2.76 mMol). The reaction mixture was stirred at room temperature for one-half hour. The reaction mixture was then diluted with 10% hydrochloric acid and extracted well with dichloromethane. The combined organic extracts were dried over sodium sulfate and concentrated in vacuo to give a viscous oil. The oil in tetrahydrofuran (5 mL) was added dropwise to a suspension of lithium aluminum hydride (110 mg, 2.76 mMol) in tetrahydrofuran (20 mL). The reaction mixture was stirred for three hours at room temperature and then one hour at reflux. The reaction mixture was then cooled to 0° C., and to it were added sequentially water (0.1 mL), 15% aqueous sodium hydroxide (0.1 mL) and water (0.3 mL). The suspension was then stirred at room temperature for two hours and then was filtered through a bed of Celite. The filtrate was concentrated in vacuo to give the title compound as a yellow viscous oil (240 mg 89%). The hydrochloride salt was formed and recrystallized (ethanol/diethyl ether) to give colorless crystals (m.p.=214°-215° C.).

Analysis: Calculated for $C_{11}H_{14}NCl \cdot HCl$: Theory: C, 56.91, H, 6.51, N, 6.03; Found: C, 57.16, H, 6.32, N, 5.87.

To a solution of racemic 2-Methylamino-8-chloro-1,2,3,4-tetrahydronaphthalene (10.0 gm, 51.3 mMol) in methanol (250 mL) was added (+)-tartaric acid (8.47 gm, 56.4 mMol), and the mixture was heated to boiling. After 10 minutes, the mixture was filtered and allowed to stand at room temperature for 18 hours. The salt that had crystallized (8.54 gm) was filtered and recrystallized from methanol (5 mL methanol/100 mg salt). The resulting solid was recrystallized from methanol four times to give a colorless crystalline solid (2.57 gm, m.p.=199°-200° C., $[\alpha]^{25}_D(H_2O) = -29.94°$). This tartarate salt was converted to the hydrochloride salt and crystalized from ethanol (m.p.=220°-221.5° C., $[\alpha]^{25}_D(-H_2O) = -64.81°$)

Analysis: Calculated for $C_{11}H_{14}NCl \cdot HCl$: Theory: C, 56.91, H, 6.51, N, 6.03; Found: C, 57.13, H, 6.30, N, 5.95.

All filtrates from the above procedure were combined and concentrated in vacuo to give a colorless solid. This solid was dissolved in water, and the solution was made basic with 15% aqueous sodium hydroxide. The solution was then extracted well with dichloromethane. The organic phases were combined, washed with water, washed with concentrated aqueous sodium chloride, dried over sodium sulfate and concentrated in vacuo to give a dark oil. The oil was then dissolved in methanol (150 mL), and to it were added (−)-tartaric acid (6.0 gm, 40 mMol). The mixture was heated until homogeneous and was then allowed to cool to room temperature. The solid recovered was recrystallized for three cycles as described above to give a colorless solid (3.24 gm, m.p.=201° C., $[\alpha]^{25}_D(H_2O) = +30.00°$ C.) This tartarate salt was converted to the hydrochloride salt and crystallized from ethanol (m.p.=220°-222° C., $[\alpha]^{25}_D(H_2O) = +64.94°$).

Analysis: Calculated for $C_{11}H_{14}NCl \cdot HCl$: Theory: C, 56.91, H, 6.51, N, 6.03; Found: C, 56.70, H, 6.25, N, 5.02.

EXAMPLE 13

Preparation of 2-Methylethylamino-8-chloro-1,2,3,4-tetrahydronaphthalene.

8-Chloro-2-methylamino-1,2,3,4-tetrahydronaphthalene (500 mg, 2.56 mMol) was reacted with acetyl chloride (0.36 mL, 5.12 mMol) and then with lithium aluminum hydride (160 mg, 4.2 mMol) as was described in Example 12 to give the title compound as a yellow oil (420 mg, 76%). The hydrochloride salt was formed and recrystallized (ethanol/diethyl ether) to give a tan solid (m.p.=177°-179° C.).

Analysis: Calculated for $C_{13}H_{18}NCl]HCl$: Theory: C, 60.01, H, 7.36, N, 5.38; Found: C, 60.22, H, 7.32, N, 5.33.

EXAMPLE 14

Preparation of 2-Methylisopropylamino-8-chloro-1,2,3,4-tetrahydronaphthalene.

To a solution of 8-chloro-2-methylamino-1,2,3,4-tetrahydronaphthalene (500 mg, 2.56 mMol) in acetone (20 mL) were added 2-iodopropane (.32 mL, 3.20 mMol) and potassium carbonate (690 mg, 5 mMol), and the mixture was heated at reflux for 68 hours. The reaction mixture was then diluted with water (80 mL) and extracted well with dichloromethane. The combined organic phases were washed with saturated aqueous sodium chloride, dried over sodium sulfate and concentrated in vacuo to give a brown residue. Purification on a basic alumina column (Activity I, dichloromethane) gave the title compound as a yellow oil (200 mg, 33%). The hydrochloride salt was formed, and recrystallization (methanol/diethyl ether) gave tan crystals (m.p.=190°-191° C.).

Analysis: Calculated for $C_{14}H_{20}NCl \cdot HCl$: Theory: C, 61.32, H, 7.72, N, 5.11; Found: C, 61.26, H, 7.67, N, 5.25.

EXAMPLE 15

Preparation of 2-Methylpropylamino-8-chloro-1,2,3,4-tetrahydronaphthalene.

To a solution of 8-chloro-2-methylamino-1,2,3,4-tetrahydronaphthalene (1.0 gm, 5.1 mMol) in acetone (50 mL) were added 1-bromopropane (.55 mL, 5.6 mMol) and potassium carbonate (1.41 gm, 10.2 mMol), and the mixture was heated at reflux for 20 hours. The reaction mixture was then cooled to room temperature, filtered and the filtrate concentrated in vacuo to give an orange oil. Purification by flash chromatography (3% methanol in dichloromethane+tr. $NH_4OH$) gave the title compound as a yellow oil (650 mg, 54%). The hydrochloride salt was formed and recrystallized (ethanol/diethyl ether) to give colorless crystals (m.p.=178°-179° C.).

Analysis: Calculated for $C_{14}H_{20}NCl \cdot HCl$: Theory: C, 61.32, H, 7.72, N, 5.11; Found: C, 61.59, H, 7.87, N, 5.09.

EXAMPLE 16

Preparation of 2-Di-n-propylamino-8-carboxamido-1,2,3,4-tetrahydronaphthalene.

To a solution of 8-bromo-2-dipropylamino-1,2,3,4-tetrahydronaphthalene (2.5 gm, 8.1 mMol) in diethyl ether (25 mL) at 0° C. was added a solution of n-butyl lithium in hexane (1.6 M, 6.3 mL, 10.1 mMol). The reaction mixture was stirred for 10 minutes at 0° C. and then for one hour at room temperature. The reaction mixture was then cannulated onto dry ice. After the dry ice had sublimed the reaction mixture was concentrated in vacuo. The residual yellow foam was then dissolved in thionyl chloride (25 mL) and stirred for three hours at room temperature. The volatiles were removed in vacuo, and liquid ammonia was added to the residue. The mixture was allowed to stand at room temperature until all of the ammonia had evaporated. The resulting residue was partitioned between chloroform and water. The organic phase was washed well with water, washed with saturated aqueous sodium chloride, dried over sodium sulfate and concentrated in vacuo to give a dark, viscous oil. Chromatography on silica gel (ethyl acetate) gave the title compound as a light yellow glass (690 mg, 31%). Crystallization (acetone/diethyl ether) gave colorless crystals (m.p.=105° C.).

Alternatively, to a solution of 8-bromo-2-dipropylamino-1,2,3,4-tetrahydronaphthalene (1.55 gm, 5 mMol) in tetrahydrofuran (35 mL) at −78° C. were added a solution of n-butyl lithium in hexane (1.6 M, 5 mL, 8 mMol), and the solution was stirred for one hour at −78° C. To the solution was then added trimethylsilylisocyanate (1 mL, 5.5 mMol), and the reaction mixture was allowed to warm gradually to room temperature. The reaction mixture was diluted with water and stirred vigorously for 10 minutes The reaction mixture was then extracted with diethyl ether. The combined extracts were dried over sodium sulfate and evaporated in vacuo to give a colorless oil. Crystallization (diethyl ether/hexane) gave the title compound as colorless crystals (880 mg, 78%, m.p.=100°-102° C.).

Analysis: Calculated for $C_{17}H_{26}N_2O$: Theory: C, 74.41, H, 9.55, N, 10.21; Found: C, 74.05, H, 9.71, N, 10.39.

EXAMPLE 17

Preparation of 2-Di-n-propylamino-8-formyl-1,2,3,4-tetrahydronaphthalene.

To a solution of 8-bromo-2-dipropylamino-1,2,3,4-tetrahydronaphthalene (1.68 gm, 5.4 mMol) in tetrahydrofuran (50 mL) at −78° C. was added a solution of n-butyl lithium in hexane (1.6 M, 5.4 mL, 8.6 mMol), and the solution was stirred for one hour at −78° C. To the solution was then added N,N-dimethylformamide (0.3 mL, 5.94 mMol), and the reaction mixture was allowed to warm gradually to room temperature. The reaction mixture was diluted with water (10 mL) and stirred vigorously for one-half hour. The reaction mixture was then extracted with chloroform. The combined extracts were washed with saturated aqueous sodium chloride, dried over sodium sulfate and evaporated in vacuo to give a yellow-green oil. Purification by flash chromatography (3% methanol in dichloromethane+tr. $NH_4OH$) gave the title compound as a colorless oil (700 mg, 50%). The maleate salt was formed and crystallized (ethanol/diethyl ether) to give colorless crystals (m.p.=120°-121° C.).

Analysis: Calculated for $C_{17}H_{25}NO \cdot C_4H_4O_4$: Theory: C, 67.18, H, 7.79, N, 3.73; Found: C, 66.94, H, 8.02, N, 3.67.

EXAMPLE 18

Preparation of 2-Propylamino-8-acetamido-1,2,3,4-tetrahydronaphthalene.

To 8-bromo-2-di-n-propylamino-1,2,3,4-tetrahydronaphthalene (500 mg, 1.6 mMol) were added acetamide (5 gm) and cuprous iodide (340 mg, 1.8 mMol), and the mixture was heated at 180° C. for four hours. The dark reaction mixture was then poured into a slurry of ice and ammonium hydroxide. This mixture was extracted well with dichloromethane, and the combined extracts were washed with water, dried over sodium sulfate and concentrated in vacuo to give a dark viscous residue. Purification by flash chromatography (3% methanol in dichloromethane+tr. $NH_4OH$) gave the title compound as a dark, viscous oil (130 mg, 31%). The maleate salt was formed and crystallized (ethanol/diethyl ether) to give tan crystals (m.p.=132°-133° C.).

Analysis: Calculated for $C_{15}H_{22}N_2O \cdot C_4H_4O_4$: Theory: C, 62.97, H, 7.25, N, 7.73; Found: C, 62.77, H, 7.49, N, 7.56.

EXAMPLE 19

Preparation of 2-Dimethylamino-8-carboxamido-1,2,3,4-tetrahydronaphthalene.

To 8-cyano-2-dimethylamino-1,2,3,4-tetrahydronaphthalene (400 mg, 1.69 mMol) were added polyphosphoric acid (2 gm) and xylene (2 mL), and the mixture was stirred at 110° C. for four hours. The reaction mixture was then poured into cold water and made strongly basic with concentrated ammonium hydroxide. The aqueous solution was then extracted with 3:1 chloroform:isopropanol, and the extracts were combined, washed with saturated aqueous sodium chloride, dried over sodium sulfate and concentrated in vacuo to give the title compound as a pale yellow, crystalline solid. Recrystallization (diethyl ether) gave colorless crystals (130 mg, 35%, m.p.=154°-155° C.).

Analysis: Calculated for $C_{13}H_{18}N_2O$: Theory: C, 71.53, H, 8.31, N, 12.83; Found: C, 74.49, H, 8.25, N, 12.72.

EXAMPLE 20

Preparation of 2-Methylethylamino-8-carboxamido-1,2,3,4-tetrahydronaphthalene.

8-Cyano-2-methylethylamino-1,2,3,4-tetrahydronaphthalene (1 gm, 4.7 mMol) was reacted with polyphosphoric acid as described in Example 19 to give, after crystallization (diethyl ether), colorless crystals (660 mg, 60%, m.p.=107°-108° C.).

Analysis: Calculated for $C_{14}H_{20}N_2O$: Theory: C, 72.38, H, 8.68, N, 12.06; Found: C, 72.30, H, 8.48, N, 11.84.

EXAMPLE 21

Preparation of 2-Di-n-propylamino-8-hydroxymethyl-1,2,3,4-tetrahydronaphthalene.

To a solution of 8-formyl-2-dipropylamino-1,2,3,4-tetrahydronaphthalene (1 gm, 3.86 mMol) in ethanol (15 mL) was added sodium borohydride (500 mg, 13.2 mMol), and the solution was stirred for 18 hours at room temperature. The reaction mixture was then diluted with water and made acidic with 10% hydrochloric acid. The aqueous was extracted once with diethyl ether, and the organic phase was discarded. The remaining aqueous phase was made basic with concentrated ammonium hydroxide and extracted with dichloromethane. The combined extracts were dried over sodium sulfate and concentrated in vacuo to give a colorless oil. Purification by flash chromatography (3% methanol in dichloromethane+tr. $NH_4OH$) gave the title compound as a colorless, viscous oil (780 mg 77%). The fumarate salt was formed and crystallized (ethanol/diethyl ether) to give colorless crystals (m.p.=151°-152° C.).

Analysis: Calculated for $C_{17}H_{27}NO \cdot C_4H_4O_4$: Theory: C, 66.82, H, 8.28, N, 3.71; Found:. C, 67.07, H, 8.47, N, 3.65.

Alternatively, a solution of 2-dipropylamino-8-methoxycarbonyl-1,2,3,4-tetrahydronaphthalene (480 mg, 1.66 mMol) in tetrahydrofuran (5 mL) was added dropwise to a suspension of lithium aluminum hydride (100 mg, 2.49 mMol) in tetrahydrofuran (10 mL), and the reaction mixture was stirred at room temperature for 2.5 hours. The reaction mixture was then cooled to 0° C., and to it were added sequentially water (0.1 mL), 15% aqueous sodium hydroxide (0.1 mL) and water (0.3 mL). The suspension was then stirred at room temperature for one-half hour and was then filtered through a bed of Celite. The filtrate was concentrated in vacuo to give the title compound as a colorless, viscous oil (400 mg, 92%). The hydrochloride salt was formed and recrystallized (ethanol/diethyl ether) to give colorless crystals (m.p.=142° C.). Analysis: Calculated for $C_{17}H_{27}NO \cdot HCl$: Theory: C, 69.02, H, 8.86, N, 4.73; Found: C, 69.03, H, 8.72, N, 4.61.

As noted above, the compounds of this invention have agonist binding affinity for the 5-$HT_{1a}$ receptor. Therefore, another embodiment of the present invention is a method of effecting agonist action at the 5-$HT_{1a}$ receptors which comprises administering to a mammal in need thereof a pharmaceutically effective amount of a compound of the invention.

The term "pharmaceutically effective amount", as used herein, represents an amount of a compound of the invention which is capable of binding to serotonin 1a receptors. The specific dose of compound administered according to this invention will, of course, be determined by the particular circumstances surrounding the case, including, for example, the compound administered, the route of administration, and the condition being treated. A typical daily dose generally will contain from about 0.01 mg/kg to about 20 mg/kg of the active compound of this invention. Preferred daily doses generally will be from about 0.05 to about 10 mg/kg, and ideally from about 0.1 to about 5 mg/kg.

The compounds can be administered by a variety of routes including oral, rectal, transdermal, subcutaneous, intravenous, intramuscular, and intranasal. A special feature of the compounds of this invention is that they are extremely selective in effecting agonist action at serotonin 1a receptors relative to other serotonin receptors.

A variety of physiologic functions have been shown to be subject to influence by brain serotonergic neural systems. As such, the compounds of this invention are believed to have the ability to treat in mammals a variety of 5-HT mediated states and disorders such as sexual disorders, eating disorders, depression, alcoholism, pain, senile dementia, anxiety, and smoking. Therefore, the present invention also provides methods of treating the above disorders at rates set forth above for agonist action in mammals at 5-HT receptors.

The following experiment was conducted to demonstrate the ability of the compounds of the present invention to effect agonist action at the serotonin 1a receptors. This general procedure is set forth in Wong et al., J. Neural Transm. 71:207–218 (1988).

Male Sprague-Dawley rats (110–150 g) from Harlan Industries (Cumberland, Ind.) were fed a Purina Chow ad libitum for at least 3 days before being used in the studies. Rats were killed by decapitation. The brains were rapidly removed, and the cerebral cortices were dissected out at 4° C.

Brain tissues were homogenized in 0.32 M sucrose. After centrifugation at 1000×g for 10 min and then at 17000×g for 20 min, a crude synaptosomal fraction was sedimented. The pellet was suspended in 100 vol of 50 mM Tris-HCl, pH 7.4, incubated at 37° C. for 10 min, and centrifuged at 50000×g for 10 min. The process was repeated and the final pellet was suspended in ice-chilled 50 mM Tris-HCl, pH 7.4. By the radio-ligand binding method, sites specifically labeled by tritiated 8-hydroxy-2-dipropylamino-1,2,3,4-tetrahydronaphthalene ($^3$H-8-OH-DPAT) have been identified as 5HT-$_{1a}$ receptors.

Binding of ($^3$H-8-OH-DPAT) was performed according to the previously described method [Wong et al., J. Neural Transm. 64:251–269 (1985)]. Briefly, synaptosomal membranes isolated from cerebral cortex were incubated at 37° C. for 10 min. in 2 ml of 50 mM Tris-HCl, pH 7.4; 10 µM pargyline; 0.6 mM ascorbic acid; and 0.4 nM $^3$H-8-OH-DPAT. Binding was terminated by filtering samples under reduced pressure through glass fiber (GFB) filters. The filters were washed twice with 5 ml of ice cold buffer and placed in scintillation vials with 10 ml of PCS (Amersham/Searle) scintillation fluid. Radioactivity was measured with a liquid scintillation spectrometer. Unlabeled 8-OH-DPAT at 10 µM was also included in separate samples to establish non-specific binding. Specific binding of $^3$H-8-OH-DPAT is defined as the difference of radioactivity bound in the absence and in the presence of 10 µM unlabeled 8-OH-DPAT.

The results of the evaluation of various compounds of the present invention are set forth below in Table I. In Table I, the first column provides the Example Number of the compound evaluated; the next three columns identify the structure of the compound evaluated when taken with the formula set forth in the heading; the next-succeeding column identifies the salt form of the compound evaluated; and the final column provides the amount of the test compound expressed in nanomolar concentration required to inhibit the binding of $^3$H-8-OH-DPAT by 50%, and is indicated in Table I as $IC_{50}$.

TABLE I

BINDING AT $5HT_{1a}$ RECEPTORS IN VITRO

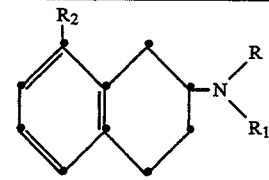

| Compound of Example No. | R | $R_1$ | $R_2$ | Salt Form | $IC_{50}(nM)$ $5HT_{1a}$ |
|---|---|---|---|---|---|
| 1 | Pr | Pr | Cl | hydrochloride | 18 |
| 2 | Et | Et | Cl | hydrochloride | 48; 38.2 |
| 3 | Allyl | Allyl | Cl | hydrochloride | 45.2 |
| 4 | n-Bu | n-Bu | Cl | tosylate | 780; 318 |
| 5 | Pr | Pr | Br | hydrochloride | 23; 15.1 |
| 6 | Pr | Pr | F | hydrochloride | 280 |
| 7 | Pr | Pr | $CH_3OCO$ | hydrochloride | 1.4; 1.8; 2.4 |
| 8 | Pr | Pr | CN | hydrochloride | 55 |
| 9 | $CH_3$ | $CH_3$ | CN | hydrochloride | — |
| 10 | Pr | H | Cl | hydrochloride | 200 |
| 11 | $CH_3$ | $CH_3$ | Cl | hydrochloride | 580; 272 |
| 12 | $CH_3$ | H | Cl | hydrochloride | — |
| 13 | $CH_3$ | $C_2H_5$ | Cl | hydrochloride | 120 |
| 14 | $CH_3$ | i-Pr | Cl | hydrochloride | — |
| 15 | $CH_3$ | Pr | Cl | hydrochloride | 500 |
| 16 | Pr | Pr | $CONH_2$ | — | 7.1; 9; 6.1; 5.8 |
| 17 | Pr | $Pr_3$ | CHO | maleate | 17.2 |
| 18 | Pr | Pr | $HNCOCH_3$ | maleate | NA |
| 19 | $CH_3$ | $CH_3$ | $CONH_2$ | — | — |
| 20 | $CH_3$ | $C_2H_5$ | $CONH_2$ | — | 400 |
| 21 | Pr | Pr | $CH_2OH$ | fumarate | 55.5 |

The compounds of this invention are also effective in reducing blood pressure. The blood pressure lowering effect of the compounds of this invention was determined in conscious spontaneous hypertensive rats (SHR; 325–425 g). The rats were anesthetized with halothane (2% in nitrous oxide and oxygen) and were implanted with femoral arterial and venous catheters. The tips of arterial and venous catheters-were positioned in the abdominal aorta below the renal arteries and lower abdominal vena cava, respectively. The catheters were routed subcutaneously to an exit point at the base of the skull and then through a small leather harness fastened around the forequarters of each animal. The animals were allowed a 3- to 4-day recovery period after surgery. On the day before an experiment, each rat was conditioned to the experimental surroundings for 6 hours. On the day of the experiment, the harness on the back of each animal was connected to a spring tether through which arterial and venous extension tubing was routed. The other end of the tubing was connected to a water tight swivel. This system permitted direct recording of blood pressure in conscious free moving animals. Mean arterial blood pressure was measured via a Statham strain gauge transducer (P23DB, Statham Instruments, Oxnard, Calif.) and recorded on a multichannel oscillograph (Beckman Model R611, Beckman Instruments, Palo Alto, Calif.). A minimum 30-minute equilibration period was observed prior to the experimental protocol during which time the animals preened and blood pressure was quite labile. Afterward, the animals appeared to sleep and pressure was stable. Following a control blood pressure measurement, rats were dosed with the compound or vehicle i.v., and pressure was monitored at various time intervals thereafter.

Table II following reports the results of these studies.

cal formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methylhydroxybenzoates, propyl hydroxybenzoates, talc, magnesium stearate, and mineral oil. The formulations may additionally include lubricating agents, wetting agents, emulsifying agents, suspending agents, preserving agents, sweetening agents, flavoring agents, and the like. The compositions of the

TABLE II

Effect On Blood Pressure And Heart Rate After I.V. Administration To Conscious SHR[1]

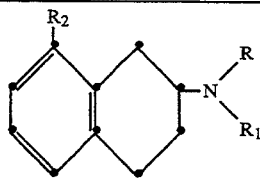

| | | | | 15 min. after Treatment | | | | | 30 min. after Treatment | | | | |
|---|---|---|---|---|---|---|---|---|---|---|---|---|---|
| | | | | Blood Pressure | | Heart Rate | | | Blood Pressure | | Heart Rate | | |
| Compound of Example No. | R | $R_1$ | $R_2$ | Corr. | $ED_{25}$, mg/kg | Corr. | $ED_{15}$, mg/kg | HR Index | Corr. | $ED_{25}$ mg/kg | Corr. | $ED_{15}$ mg/kg | HR Index |
| 1 | Pr | Pr | Cl | 0.97 | 3.1 | 0.90 | 27.8 | 8.96 | 0.98 | 13 | 0.97 | 2.8 | 0.22 |
| 2 | Et | Et | Cl | 0.72 | — | 0.30 | — | — | 0.98 | 1.5 | 0.92 | 1.5 | 1.00 |
| 5 | Pr | Pr | Br | 2 pt | 6.1 | 2 pt | 1.6 | 0.06 | 2 pt | 5.9 | 2 pt | 1.6 | 0.27 |
| 6 | Pr | Pr | F | 2 pt | 4.5 | 2 pt | Pos | 2 pt | >3 g. | — | 2 pt | 8.0 | — |
| 7 | Pr | Pr | CH$_3$OCO | 0.49 | | 0.99 | 1.4 | — | 0.89 | 5.3 | 0.99 | 1.1 | 0.21 |
| 8 | Pr | Pr | CN | 2 pt | 5.1 | 2 pt | 3.6 | 0.71 | 2 pt | 4.1 | 2 pt | 2.8 | 0.68 |
| 10 | Pr | H | Cl | 0.99 | 2.5 | 0.97 | 1.2 | 0.48 | 0.99 | 4.5 | 0.97 | 2.1 | 0.47 |
| 11 | CH$_3$ | CH$_3$ | Cl | 0.98 | 1.1 | 0.98 | 1.1 | 1.0 | 0.99 | 1.8 | 0.88 | 5.4 | 3.00 |
| 12 | CH$_3$ | H | Cl | 0.99 | 1.4 | 0.29 | — | — | 0.99 | 1.8 | 0.81 | 1.5 | 0.83 |
| 13 | CH$_3$ | C$_2$H$_5$ | Cl | 0.99 | 0.7 | 0.99 | 0.48 | 0.69 | 0.96 | 0.9 | 0.97 | 0.63 | 0.70 |
| 14 | CH$_3$ | i-Pr | Cl | 0.97 | 2.9 | 0.99 | 3.8 | 1.31 | 0.99 | 6.1 | 0.86 | 2.1 | 3.34 |
| 15 | CH$_3$ | Pr | Cl | 0.99 | 1.6 | (non-linear heart rate) | | | 0.98 | 3.8 | — | — | — |
| 16 | Pr | Pr | CONH$_2$ | 0.99 | 4.2 | 0.99 | 1.5 | 0.35 | 0.82 | 5.7 | 0.91 | 2.9 | 0.51 |
| 18 | Pr | H | HNCOCH$_3$ | — | NA[2] | 2 pt | 3.8 | — | — | — | 2 pt | 1.2 | — |
| 19 | CH$_3$ | CH$_3$ | CONH$_2$ | 2 pt | 10.9 | 2 pt | Pos | | 2 pt | 1031 | 2 pt | Pos | — |
| 21 | Pr | Pr | CH$_2$OH | 0.86 | 4.2 | 0.60 | — | — | 0.72 | — | 0.51 | —[3] | — |

[1]Standard protocol recorded the blood pressure and heart rate responses after 0.3, 1.0 and 3.0 mg/kg i.v. Dose response curves were plotted using the % change in pressure from pretreatment control values at 15 and 30 minutes after treatment.
Corr = correlation coefficient for the linear relationship between the log dose(s) and % change (y) in pressure. Values of 1.0 = perfect correlation.
Pos = Positive slope of dose response
$ED_{25}$ = i.v. dose required to decrease pressure 25%
HR Index = $ED_{15}$ for Heart Rate divided by $ED_{25}$ for Blood Pressure.
[2]Inactive at 0.3, 1.0 mg/kg.
[3]3.0 mg/kg caused convulsion.

The compounds of this invention are preferably formulated prior to administration. Therefore, another embodiment of the present invention is a pharmaceutical invention may be formulated so as to provide quick, sustained or delayed release of the active ingredient after administration to the patient by employing procedures well known in the art.

The compositions are preferably formulated in a unit dosage form, each dosage generally containing from about 0.1 to about 500 mg, and preferably from about 1 to about 250 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

|  | Quantity (mg/capsule) |
| --- | --- |
| 2-di-n-propylamino-8-chloro-1,2,3,4-tetrahydronaphthalene hydrochloride | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
| --- | --- |
| 2-di-n-propylamino-8-hydroxymethyl-1,2,3,4-tetrahydronaphthalene hydrochloride | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

|  | Weight % |
| --- | --- |
| 2-diisopropylamino-8-carboxamido-1,2,3,4-tetrahydronaphthalene dihydrochloride | 0.25 |
| ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 3

Tablets, each containing 60 mg of active ingredient, are made as follows:

| 2-methylethylamino-8-formyl-1,2,3,4-tetrahydronaphthalene maleate | 60 mg |
| --- | --- |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| 2-propylamino-8-acetamido-1,2,3,4-tetrahydronaphthalene hydrochloride | 80 mg |
| --- | --- |
| starch | 59 mg |
| microcrystalline cellulose | 59 mg |
| magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| 2-di-n-propylamino-8-cyano-1,2,3,4-tetrahydronaphthalene hydrochloride | 225 mg |
| --- | --- |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| 2-diallylamino-8-methoxycarbonyl-1,2,3,4- | 50 mg |
| --- | --- |

| | |
|---|---|
| tetrahydronaphthalene hydrochloride | |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| 2-diethylamino-8-bromo-1,2,3,4-tetra-hydronaphthalene hydrochloride | 100 mg |
| isotonic saline | 1000 ml |

The solution of the above ingredients generally is administered intravenously at a rate of 1 ml per minute to a subject suffering from depression.

We claim:

1. A compound of the formula:

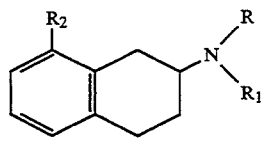

in which R is allyl;
$R^1$ is hydrogen, $C_1$-$C_4$ alkyl, or allyl;
$R^2$ is halo;
and pharmaceutically acceptable acid addition salts thereof.

2. Compound of claim 1, in which $R_1$ is $C_1$-$C_4$ alkyl.
3. Compound of claim 2, in which $R_1$ is n-propyl.
4. Compound of claim 1, in which $R_2$ is selected from chloro or bromo.
5. Compound of claim 4, in which $R_2$ is chloro.
6. Compound of claim 4, in which $R_2$ is bromo.
7. A pharmaceutical formulation which comprises, in association with a pharmaceutically acceptable carrier, diluent, or excipient, a compound of the formula

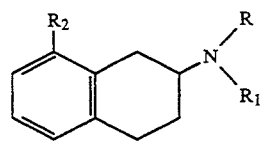

in which R is allyl;
$R_1$ is hydrogen, $C_1$-$C_4$ alkyl, or allyl;
$R_2$ is halo;
and pharmaceutically acceptable acid addition salts thereof.

8. A racemate or stereo isomer of the compound of the formula

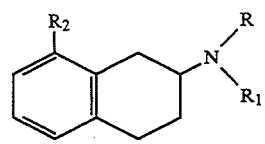

in which R is $C_1$-$C_4$ alkyl;
$R_1$ is hydrogen or $C_1$-$C_4$ alkyl;
$R_2$ is halo;
and pharmaceutically acceptable acid addition salts thereof.

9. A compound of claim 8, in which $R_2$ is chloro.
10. A compound of claim 8, in which $R_2$ is bromo.
11. A compound of claim 8, in which $R_1$ is $C_1$-$C_4$ alkyl.
12. A compound of claim 11, in which R and $R_1$ are n-propyl.
13. A compound of claim 10, in which R and $R_1$ are n-propyl.
14. A pharmaceutical formulation which comprises a compound of claim 8, or a pharmaceutically acceptable salt thereof, in association with a pharmaceutically acceptable carrier, diluent or excipient therefor.
15. Formulation of claim 14, in which the compound is 2-di-n-propylamino-8-chloro-1,2,3,4-tetrahydronaphthalene or a pharmaceutically acceptable acid addition salt thereof.
16. Formulation of claim 14, in which the compound is 2-di-n-propylamino-8-bromo-1,2,3,4-tetrahydronaphthalene or a pharmaceutically acceptable acid addition salt thereof.
17. A compound of claim 8, which is the racemate.
18. A compound of claim 8, which is the d-stereoisomer.
19. A compound of claim 8, which is the l-stereoisomer.

* * * * *

UNITED STATES PATENT AND TRADEMARK OFFICE
CERTIFICATE OF CORRECTION

PATENT NO.    : 5,389,687

DATED         : February 14, 1995

INVENTOR(S)   : John M. Shaus et al.

It is certified that an error appears in the above-identified patent and that said Letters Patent is hereby corrected as shown below:

Column 10, line 29, "(500 rag)" should read, -- (500 mg) --.

Column 15, line 67, and Column 16, lines 7 and 28, "($^8$H-8-OH-DPAT)" should read, -- ($^3$H-8-OH-DPAT) --.

Columns 17-18, Table II, Example 14 under HR Index, "3.34" should read, -- 0.34 --.

Column 20, line 2, "Formulation 3" should read, -- Formulation 4 --.

Column 22, line 23, "$C_1C_4$ alkyl" should read, -- $C_1$-$C_4$ alkyl --.

Signed and Sealed this

Tenth Day of October, 1995

Attest:

BRUCE LEHMAN

*Attesting Officer*    *Commissioner of Patents and Trademarks*